United States Patent [19]
Barlian et al.

[11] Patent Number: 4,553,432
[45] Date of Patent: Nov. 19, 1985

[54] TEMPERATURE-HUMIDITY SURVEILLANCE EQUIPMENT

[75] Inventors: Reinhold Barlian, Dieselstrasse 6, D-6990 Bad Mergentheim, Fed. Rep. of Germany; Martin Fischle, Bad Mergentheim, Fed. Rep. of Germany

[73] Assignee: Reinhold Barlian, Bad Mergentheim, Fed. Rep. of Germany

[21] Appl. No.: 512,444

[22] Filed: Jul. 11, 1983

[30] Foreign Application Priority Data

Jul. 10, 1982 [DE] Fed. Rep. of Germany ....... 3225921

[51] Int. Cl.⁴ ...................... G01N 25/64; G01N 27/14
[52] U.S. Cl. ..................................... 73/336; 73/336.5; 219/505; 338/35; 340/602; 374/142
[58] Field of Search ............... 374/101, 110; 73/336.5; 338/26, 27, 14; 174/11 R, 115

[56] References Cited

U.S. PATENT DOCUMENTS

| | | | |
|---|---|---|---|
| 3,520,476 | 7/1970 | Schmid | 338/14 X |
| 3,588,776 | 6/1971 | Horwinski | 174/115 X |
| 3,825,669 | 7/1974 | Korner et al. | 174/11 R |
| 4,013,924 | 3/1977 | Christensen et al. | 174/11 R X |
| 4,029,889 | 6/1977 | Mizuochi | 174/11 R |
| 4,206,632 | 6/1980 | Suzuki | 73/40.5 R |
| 4,246,468 | 1/1981 | Horsma | 219/505 X |
| 4,319,485 | 3/1982 | Terada et al. | 73/336 |
| 4,386,231 | 5/1983 | Vokey | 174/115 |
| 4,419,021 | 12/1983 | Terada et al. | 374/142 X |
| 4,420,974 | 12/1983 | Lord | 374/185 |

FOREIGN PATENT DOCUMENTS

| | | |
|---|---|---|
| 0073322 | 3/1983 | European Pat. Off. . |
| 57-10429 | 1/1982 | Japan ................................ 374/111 |

Primary Examiner—Daniel M. Yasich
Attorney, Agent, or Firm—Horst M. Kasper

[57] ABSTRACT

A surveillance device is provided for a container filled with a fluid or the like and it includes an electrical resistance wire for temperature control and a hygroscopic insulator for control of humidity. For this purpose, an electrical conductor wire is disposed substantially in parallel to the resistance wire in its longitudinal direction, which forms together with the resistance wire and the hygroscopic insulator a single unit multifunctional temperature-humidity measurement cable. At least two essentially parallel running wire conductor strands are provided for a potential-free and mutually noninterfering measurement. The hygroscopic insulator is disposed between the wire conductor strands. The cable sensor can be employed in power and steam plants and in nuclear installations.

57 Claims, 20 Drawing Figures

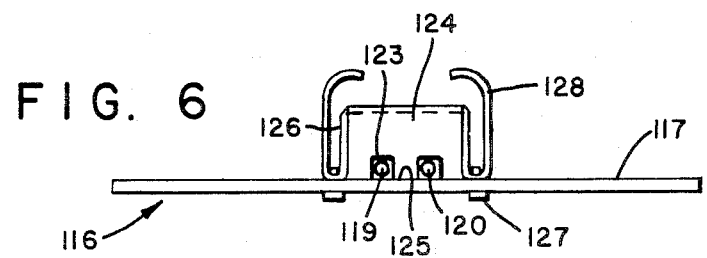
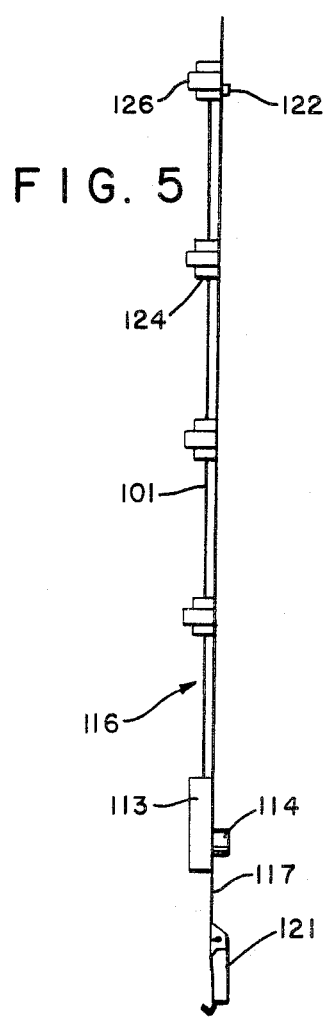
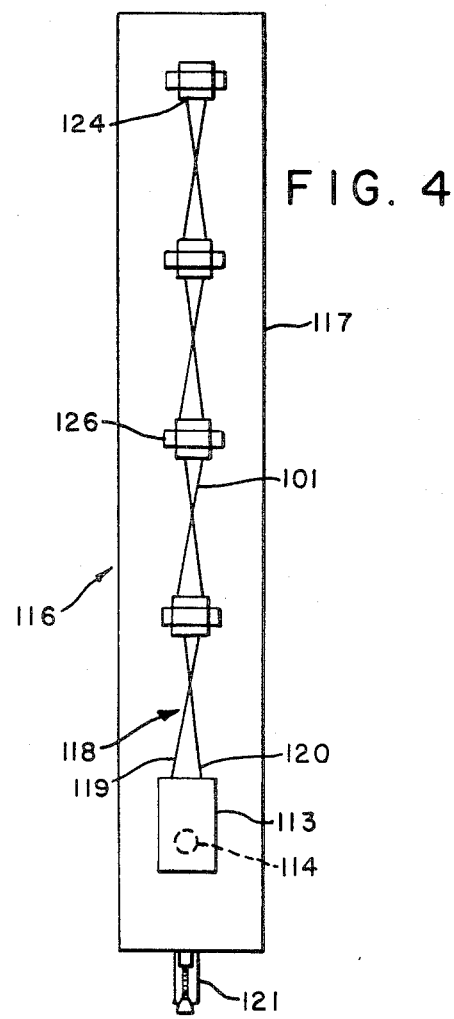

TEMPERATURE-HUMIDITY SURVEILLANCE EQUIPMENT

BACKGROUND OF THE INVENTION

1. Field of the Invention

The present invention relates to a surveillance provision and a surveillance method for a container filled with a fluid and in particular for a steam pipe, where an electrical resistance wire provides temperature control and a hygroscopic insulator provides humidity control.

2. Brief Description of the Background of the Invention Including Prior Art

Temperature control and humidity control have been provided for example according to German Patent Application DE 3,127,244.4-52, where an electrical conductor wire is disposed next to a resistance wire in its longitudinal direction under continuous maintenance of a distance spacing by a hygroscopic insulator. A multifunctional temperature-humidity measurement cable is provides as a single construction unit with the resistance wire and the hygroscopic insulator. The present invention is an improvement over published German Patent Application 3,127,244.4-52, the contents of which is hereby included in this application by reference.

SUMMARY OF THE INVENTION

Purposes of the Invention

It is an object of the present invention to provide an improved surveillance provision for fluids in containers, where there is excluded a mutual interaction of the temperature and humidity measurement.

It is a further object of the present invention to provide a temperature-humidity measurement system where the measurement is substantially potential free and interference protected.

It is a further object of the present invention to provide a temperature-humidity measurement cable which operates reliably and which can be produced economically.

These and other objects and advantages of the present invention will become evident from the description which follows.

BRIEF DESCRIPTION OF THE INVENTION

The present invention provides a surveillance provision for containers of fluids which comprises a first electrical conductor wire, a second electrical conductor wire running substantially parallel to the first electrical conductor wire, a hygroscopic insulator means disposed between the first and the second electrical conductor wires for providing humidity control, a resistance wire running about along the electrical conductor wires and disposed at a spaced distance from the first and the second electrical conductor wires by way of the hygroscopic insulator means.

The container can be a steam pipe. The hygroscopic insulating means can depend on humidity and the electrical conduits, the hygroscopic insulating means, and the resistance wire can be provided as a multifunctional temperature-humidity test lead. The electrical conductor wires can be provided as stranded wires made from thin individual wires. The hygroscopic insulator means of the temperature-humidity cable can be provided as a jacket surrounding at least one of the electrical conducting wires. The hygroscopic insulating means can comprise glass filament insulation. The hygroscopic insulating means can be provided as a woven, braided glass filament tube surrounding at least one of the electrical conductor wires.

A humidity permeable insulator can surround the hygroscopic insulating means and the electrical conductor wires and the electrical conductor wires can be strands of thin wires. The insulator surrounding the electrical conductor wires and the hygroscopic insulating means can be a fabric tube formed from glass filaments. The resistance wire of the temperature-humidity measurement cable can be disposed spirally around the insulator surrounding the stranded wires of the electrical conductor wires and the hygroscopic insulating means.

A humidity permeable outer jacket can surround the two electrical conductor wires and the hygroscopic insulating means can be disposed in the insulator and the resistance wire. The outer jacket of the temperature-humidity measurement cable can be provided as a braided glass filament tube. A return line can be coordinated to the resistance wire for the temperature measurement, which is connected to the end of the resistance wire with a fused metal connection and which is temperature stable insulated. The return line preferably is disposed on the outside of the temperature-humidity measurement cable and the insulation of the return line is provided by a member of the group consisting of tetrafluoroethylene (Teflon), glass filaments, and mixtures thereof. The return line of the resistance wire can be provided by a stranded copper wire disposed inside of the outer jacket and running substantially in parallel to the electrical conductor wire strands. The return line of the resistance wire can be provided substantially as a braided cover. A base load resistor can be coordinated to the electrical conductor wires of the temperature-humidity measurement cable for humidity detection and/or rupture surveillance. The base load resistor can be disposed between the two stranded electrical wire conductors at the end opposite to the connection point of the temperature-humidity measurement cable.

The temperature-humidity measurement cable can be provided with a connector part provided as a multipole receptacle. Preferably, the temperature-humidity cable is disposed substantially free in the region of a stuffed solid insulation in the longitudinal direction and/or surface direction of the steam pipe between the wall of a steam pipe and an outer covering. A flat band can support the temperature-measurement cable. The flat band can be provided with a toggle type fastening clamp adjustable in small steps. Preferably, the temperature-humidity cable is fixed in a desired position via a clamping block attached to the flat band. The temperature-humidity cable can be guided by at least one longitudinal groove of the clamping block. The temperature-humidity measurement cable can be disposed with a feed cable part and a return cable as a cable loop at the flat band. The clamping block can have two substantially parallel longitudinal grooves for receiving the feed cable and the return cable. Preferably, the clamping block comprises an elastic and temperature resistant insulating material such as silicon caoutchouc.

An insulating foil can be disposed at least in the region of the clamping block between the temperature-humidity measurement cable and the flat band. Preferably, the clamping block is fixed with a clamp strap at the flat band. The temperature-humidity measurement cable can be attached to the flat band by way of several clamping blocks disposed at a distance in the longitudinal direction and the feed cable and the return cable can run crossing over between two clamping blocks. A connector block from cast resin can shield against humidity and can insulate electrically, which connector block seals the temperature-humidity measurement cable in the region of the receptacle. Preferably, the connector block is disposed in the longitudinal direction of the flat band substantially within a plane with the clamping block or, respectively, clamping strap and has about the same width as the clamping strap.

The temperature-humidity measurement cable can be disposed at the region of a butt connection of the thermal insulation, where the flat band covers the groove adjoining the butt connection and where the flat band is secured in the groove by way of side limiting webs of the engaging clamping straps against a sideways shift. A sealing strip can be provided between the flat band supporting the temperature-humidity cable and the covering of the thermal insulation. The bordering wall of the groove can be provided with at least one inclined part extending essentially from the bottom of the groove in the region of the butt connection of the thermal insulation.

A subsidiary distributing box can be connected to the temperature-humidity measurement cables of different surveillance positions. An electronic measurement value processing unit can include measurement transformers for evaluating and monitoring of temperature and humidity. Preferably, a control computer system is coordinated to the measurement processing unit connected to the temperature-humidity measurement cable which comprises two independent microcomputers for providing data collection, interference reporting and printer control. An alarm provision can be coordinated to the measurement processing unit of the temperature-humidity measurement cable. Preferably, a picture providing representation installed at an operating desk of a power plant and associated with the measurement value processing of the temperature-humidity measurement cable.

The temperature-humidity measurement cable can be employed in a gully in the floor of a power plant for the detection of the presence of liquids. The temperature-humidity measurement cable can be disposed at an insertion body placed into the gully. From a contact to only a slight gap can be present between a container wall and the temperature-humidity measurement cable disposed at the insertion body. Desirably, the temperature-humidity measurement cable is disposed at a circumferential recess of the insertion body such that the outer diameter is equal to or slightly larger than the diameter of the insertion body in the region of the temperature-humidity measurement cable. The connection of the temperature-humidity cable can be furnished substantially as a construction unit with a liquid sealing coupling plug of a measurement conduit disposed in a liquid sealing insulated receptacle in the insertion body. The plug receptacle can be maintained in the middle region of the insertion body via radial steadying support struts. The insertion body with the temperature-humidity measurement cable can be supported in a tubular container part, which is disposed at a ring insertable into the gully. The tubular container part can be disposed substantially off center at an inner surface of the ring and is provided here with a groove formation for feeding in of the liquid. Preferably, a measurement processing unit comprising transducers, evaluation electronics, control systems and an alarm provision is coordinated to the temperature-humidity measurement cable disposed at the insertion body located in the gully.

If necessary, an electrical voltage can be applied to the resistance wire of the temperature-humidity measurement cable such that the resistance wire is formed as an electrical heating element for the drying of possible humidity parts in the temperature-humidity measurement cable or in its environment.

There is further provided a method for surveillance of a container containing a fluid medium, which comprises separating two substantially parallel running electrical conductor wires with an interposed hygroscopic insulating means for humidity control, surrounding the wires and the hygroscopic insulating means with an insulator, running substantially in parallel to the electrical conductor wires a resistance wire at a distance, and covering the wires and insulation in order to obtain a temperature-humidity measurement cable.

The hygroscopic insulating means can be provided as glass filament insulation. The temperature-humidity measurement cable can be attached to a flat band. A sealing strip can be attached between the flat band carrying the temperature-humidity measurement cable and the covering of the thermal insulation. The temperature-measurement cable can be surrounded with an insertion body, and the insertion body can be placed in a gully.

The novel features which are considered as characteristic for the invention are set forth in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

In the accompanying drawing, in which are shown several of the various possible embodiments of the present invention:

FIG. 4 is a view from below of a detection band, FIG. 5 is a side view of the detection band according to FIG. 4, FIG. 6 is an enlarged sectional view of the detection band according to FIG. 4.

DESCRIPTION OF INVENTION AND PREFERRED EMBODIMENTS

Figure 1:
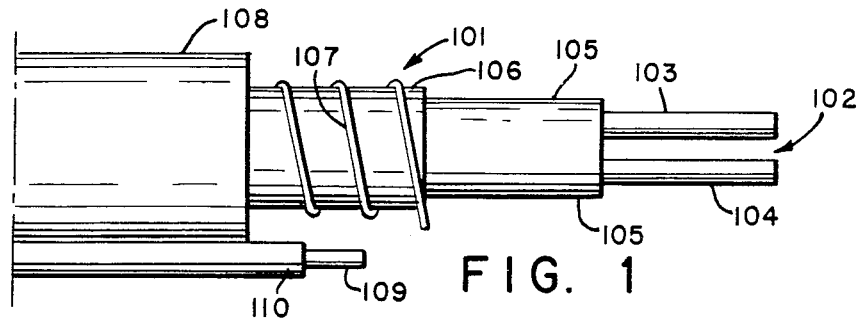
FIG. 1 is a side elevational view of part of a temperature-humidity measurement cable according to the invention on an enlarged scale.

In accordance with the present invention there is provided a surveillance system for a container comprising a medium or receiving a medium and in particular for a steam pipe, with an electrical resistance wire serving to monitor temperature and a hygroscopic insulator depending on humidity such as set forth in published German Patent Application P 3,127,244.4-52, where an electrical conductor is disposed next to the resistance wire in its longitudinal direction under providing a continuous distance spacing with the hygroscopic insulator and where the resistance wire as well as the hygroscopic insulator are formed as a one unit multifunctional temperature-humidity measurement cable and where the conductor 102 of the temperature-humidity measurement cable 101, 111 is formed from at least two conductor wire stands 103, 104 running substantially in parallel, between which the hygroscopic insulator 105 is disposed for humidity control.

The conductor wire strands 103, 104 of the conductor wire 102 can be provided as stranded wire from thin individual wires. The hygroscopic insulator 105 of the temperature-humidity measurement cable 101, 111 can be formed as a covering for at least one of the two conductor wire strands 103, 104 of the conductor wire 102. The hygroscopic insulator 105 surrounding the wire conductor strand 103, 104 of the conductor 102 can comprise a glass filament insulation. The hygroscopic insulator of the wire conductor strand 103, 104 forming the conductor 102 can be formed as a woven, plaited or braided glass filament tube surrounding the latter. The two wire conductor strands 103, 104 of the conductor 102 and the intermediately disposed hygroscopic insulator 105 can be surrounded by a humidity permeable insulator 106. The insulator combining the conductor wire strands 103, 104 and the hygroscopic insulator 105 can be a fabric tube formed from glass filament. The resistance wire 107 of the temperature-humidity measurement cable 101, 111 can be substantially spirally or helically wound around the insulator 106 surrounding the wire conductor strands 103, 104 of the conductor 102 and the hygroscopic insulator.

A humidity permeable outer wall 108 can combine the two wire conductor strands 103, 104 of the conductor 102, the hygroscopic insulator 105, the insulator 106 surrounding the wire conductor strands 103, 104 and the hygroscopic insulator 105, and the resistance wire 107. The outer jacket 108 of the temperature-humidity measurement cable 101, 111 can be provided as a woven, plaited or braided tube from glass filaments.

A return conductor 109, 112, etc., can be coordinated to the resistance wire 107 for the temperature measurement, which is preferably by welding, brazing or soldering connected to the end of the resistance wire 107 and is temperature resistant insulated. The return conductor 109 of the resistance wire 107 can be disposed or, respectively, supported on the outside of the temperature-humidity test cable 101 and is preferably provided with a Teflon or glass fiber insulation.

The return conductor 112 of the resistance wire is preferably provided by a strand of copper wires and is disposed running substantially parallel to the conductor wire strands 103, 104 in the outer jacket 108 of the temperature-humidity measurement cable 111. The return conductor of the resistance wire 107 can be provided essentially as a braided cover. A base load resistor 115 can be coordinated to the conductor wire 102 of the temperature-humidity measurement cable 101, 111 for humidity detection and/or rupture surveillance. The base load resistor 115 can be disposed between the two wire conductor strands 103, 104 preferably at the end remote relative to the connection of the temperature-humidity measurement cable. The temperature-humidity measurement cable 101, 111 is provided with a connection part preferably in the form of a multipole receptacle. The temperature-humidity measurement cable 101, 111 is preferably substantially unlimited free disposed or, respectively, installed in longitudinal direction and/or circumferential direction in the region of a stuffed solid insulation in particular between a wall of the steam pipe and an outer covering 131.

Preferably, the temperature-measurement cable 101 is disposed at a flat band 117. The flat band 117 can be provided with a toggle type fastening clamp 121 substantially adjustable in small steps. The temperature-humidity measurement cable 101 preferably is fastened at the flat band 117 via a clamping block 124. Preferably, the temperature-humidity measurement cable is guided in at least one longitudinal groove 123 of the clamping block. The temperature-humidity measurement cable 101 can be disposed with a feed cable part 119 and a return cable part 120 as a cable loop 118 at the flat band 117. The clamping block 124 can be provided with two essentially parallel longitudinal grooves 123 for receiving the feed cable part 119 and the return cable part 120. The clamping block 124 preferably comprises an elastic and temperature stable insulating material such as for example silicone caoutchouc. An insulating foil 125 is disposed at least in the region of the clamping block 124 between the temperature-humidity measurement cable 101 and the flat band 117. The clamping block 124 can be fixed in position with a clamping strap 126 at the flat band 117. The temperature-humidity measurement cable 101 can be attached at the flat band 117 in longitudinal direction with several clamping blocks 124 disposed at a distance. The feed line 119 and the return line 120 can cross over between two clamping blocks.

The connection of the temperature-humidity measurement cable 101 in the region of the receptacle 114 can be sealed with a humidity shielding and electrically insulating connection block 113 preferably made from cast resin. The connection block 113 can be disposed in longitudinal direction of the flat band 117 substantially in a plane with the clamping block 124 or, respectively, clamping strap 126 and the clamping block has about the same width as the clamp strap 126. The temperature measurement cable 101 attached to the flat band 117 can be disposed in the region of a butt joint 129 of the thermal insulation 130, where the flat band 117 covers the groove 133, 134 adjoining the butt joint 129 and is secured in the groove against sideway shifting by way of side limiting webs 128 of the engaging clamping straps.

A sealing strip 136 can be provided between the flat cable carrying the temperature-humidity measurement cable and the covering of the thermal insulation. The limiting wall of the groove 134 is provided with an inclined part extending from the base of the groove in the region of the butt joint 129 of the thermal insulation in the direction of the side wall of the flat band 117. Several temperature-humidity measurement cables 101 of different surveillance stations can be connected to a subsidiary distribution box 139.

An electronic measurement processing unit 140 with transducers 146, 147 can be coordinated to the temperature-humidity measurement cable 101 for processing and evaluating the data relative to temperature and humidity. A control computer system 141 with preferably two microprocessors for data collection, interferences and printer control is coordinated to the measurement processing unit 140 with the temperature-humidity measurement cable 101. An alarm unit 142 can be coordinated to the measurement processing unit 140 of the temperature-humidity measurement cable.

A flow chart representation 143 and/or a picture screen representation 144 preferably located in a control room of a power plant can be coordinated to the measurement processing 140 of the temperature-humidity measurement cable 101.

The temperature-humidity measurement cable 101 can be employed for liquid detection in a gully disposed preferably in the floor of a room of a power plant. The temperature-humidity measurement cable 101 can be disposed at an insertion body 173, 183 located in a gully 171. A mechanical contact or only a small slot can exist between a container wall 175, 188 and the temperature-humidity measurement cable 101 disposed at the insertion body 173, 183. The temperature-humidity measurement cable 101 can be supported in a circumferential recess 176, 184 of the insertion body 173, 183 such that the outer diameter is equal to or slightly larger than the diameter of the insertion body 173, 183. The connection of the temperature-humidity measurement cable 101 with one receptacle 177 disposed sealed against liquid passage in the insertion body 173, 183 is provided as substantially one building component for a plug 179 of a test lead 180 capable of providing a connection sealing against passage of liquids. The receptacle 177 can be supported substantially in the middle region of the insertion body 173 via radial support steadying struts 178.

The insertion body 183 with the temperature-humidity measuring cable 101 can be disposed in a tubular container part 185, which is disposed at the ring 186 insertable into the gully 171. The tubular container part 185 with the insertion body 183 carrying the insertion body 183 with the temperature measurement cable 101 can be disposed substantially off center at an inner face of the ring 126 and can be provided here with a groove formation for feeding in liquid. A measurement processing unit comprising preferably transducers, evaluation electronics, control systems, alarm provisions and the like can be coordinated to the temperature-humidity measurement cable 101 disposed at the insertion body 173, 183 located in the gully 171.

An electrical voltage can be fed to the resistance wire 107 of the temperature-humidity measurement cable 101, 111 in case of need such that the resistance wire 107 is formed as an electrical heating element for the drying of possible humidity parts in the temperature-humidity measurement cable 101, 111 and/or in its environment.

Thus the temperature and humidity control and surveillance is performed with this surveillance provision via the temperature-humidity measurement cable combined to one building unit. Here the temperature determination is performed via the resistance wire 107, while the humidity measurement is performed exclusively via the two wire conductor strands 103 and 104 provided preferably from copper such that the two measurement systems are separated from each other that they cannot mutually influence each other. Therefore, a simple sensor cable is provided for several measurement functions, which assures reliable and potential free measurements. The invention temperature-humidity measurement cable can be produced under advantageous cost conditions based on its continuous production possibility in longitudinal direction and also it is provided with a long lifetime, since no wearing parts are present, but only a compact cable strand is provided. Since the temperature-humidity measurement cable has only a small total diameter, only little space is needed for mounting at the steam pipe or other measurement locations. Therefore, the temperature-humidity measurement cable can always optimally be adapted to mounting conditions or be installed to meet the requirements in each case. The temperature-humidity measurement cable allows a potential-free permanent surveillance even over relatively large distances as well as at a plurality of test locations.

In addition, the temperature-humidity measurement cable is very sensitive, which allows to recognize and detect a possible leak already at an early stage and with a low flow rate. The temperature-humidity measurement cable is practically free of service requirements based on the unified construction of a multiple function strand formation, since no individual components or the like have to be adjusted or exchanged. As soon as in case of a leak the hot fluid exits through the wall of the tube, jacket or the like, a temperature change occurs in the region of the temperature-humidity measurement cable, which is captured immediately by the resistance wire. At the same time a humidity enrichment occurs in the hygroscopic insulator between the two strands of wire conductor. The resistance change between the wire conductor strands associated therewith (Meg-ohm range) is also captured and put to use. Since the two different parameters as temperature and humidity are measured, a highly reliable surveillance and alarm production is achieved. The alarm release can without difficulty be designed such that a warning signal is only produced if a change of the two measurement factors (temperature and humidity) occurs.

The wire conductor strands in the temperature-humidity measurement cable are advantageously provided as strands, which are formed from thin copper wires such that a practical flexibility is achieved. Advantageously, the hygroscopic insulator can be provided as a covering in the form of a woven, plaited or braided glass filament insulation tube into which the wire conductor strands are combined. Advantageously, the resistance wire of the temperature-humidity measurement cable can be applied to the insulator combining the wire conductor strands, where it is advantageous to wind this resistance wire spirally or helically on the insulator. In order to achieve an outer total closure, the temperature-humidity measurement cable can be provided with an outer shell, which is permeable to humidity and which is advantageously provided as a braided, woven or plaited glass filament tube. The above described glass filament insulators effect not only a high stability and strength against outer mechanical loadings but are in addition substantially resistant to other materials and assure in addition a high temperature stability during continuous application.

In order to influence substantially the sensitivity of the humidity measurement system or in order to substantially adapt it to the requirements, it is advantageous to coordinate to the conductor wire or, respectively, to the two wire conductor strands a so-called base load resistor, which is useful both for the humidity detection as well as for the purpose of a wire rupture supervision, where the base load resistance between the two wire conductor strands is preferably provided at the end of the temperature-humidity measurement cable, which is at least electrically remote from the connection point. Preferably a four pole receptacle is provided for the connection of the temperature-measurement cable, into which a corresponding plug of a measurement line is inserted preferably safe against dust and humidity.

In addition, it can be advantageous to provide a return line for the resistance wire, which is preferably connected to the end of the resistance wire with a soldered or a welded connection. The return conductor advantageously is provided with a temperature resistant insulation, which for example can comprise Teflon or glass filaments. According to this embodiment the resistance or, respectively, resistance change between the start of the resistance wire and the end of the resistance wire is taken for the measurement of the temperature, where the return of from the outer end of the connection of the temperature-humidity measurement cable is performed by the return conductor. The return conductor can be disposed on the outside at the temperature-humidity measurement cable and can be attached at the latter for example by way of elastic or, respectively, rubberlike support rings. The return conductor predominantly comprises a copper wire strand, which can also run inside of the outer shell of the temperature-humidity measurement cable substantially parallel to the wire conductor strands, where the return conductor can be disposed both in the region between the resistance wire and the outer shell as well as in the region immediately next to the wire conductor strands. The temperature-humidity measurement cable can be placed freely in the region of an in particular stuffed heat insulation for example according to the simplest embodiment such that it extends both in longitudinal direction as well as in circumferential direction of the stream pipe or, respectively, of the container or the like. A preferred position is seen in the region between the wall of the steam pipe and the outer covering of the thermal insulation next to the interior face of the covering, where however as already set forth in principle no limitations are provided such that corresponding to the local requirements in each case an optimal installation of the temperature-humidity measurement cable can be performed for a problem-free leakage detection.

Furthermore, it can be particularly advantageous to dispose the temperature-humidity measurement cable at a flat band, which is in so far flexible that it can be for example like a clamping band wound around a tube or, respectively, its heating insulation. The flat band can in a high value performance be made from antimagnetic stainless steel and it can be provided with a toggle-type fastener clamp, which is essentially readjustable in small steps such that upon mounting to the steam pipe possible differences in the thermal insulation can be balanced without a problem, whereby in each case a fitted seat of the clamping strap and thus also of the temperature-humidity measurement cable can be assured free from problems. The attachment of the temperature-humidity measurement cable can advantageously be provided via a clamping block, which can be produced for example from an elastic and temperature resistant silicone caoutchouc and which is attached to the flat band with a clamping strap.

The clamping block can be provided with one or also two longitudinal grooves wherein the temperature-humidity measurement cable is disposed and guided, where at one temperature-humidity measurement cable disposed looped at the flat band there is disposed in the one longitudinal groove the feed cable part and in the other groove the return cable part of the temperature-humidity measurement cable. In order to assure a freedom from potentials also versus possible external influences, an insulating foil can be provided between the clamping block and the flat band such that the outer shell of the temperature-humidity measurement cable does not pass in the region of the clamping block itself upon a pressure loading into immediate contact with the flat band. The insulating foil can be made from a polyimide such as the product sold under the trademark Kapton or the like. The clamping strap for the clamping block can be detachably mounted at the clamping strap by way off screws. However, it is also possible to attach the clamping strap by way of rivets or by spot welding. The clamping strap can be provided on the two sides with limiting straps, the free ends of which are preferably inclined bent or, respectively, rounded for a problem-free insertion into the groove. The clamping blocks and the clamping straps can be disposed at distances of about 15 centimeters from each other in the longitudinal direction of the flat band in its middle region. If the temperature-humidity measurement cable is provided here as a cable loop with a feed cable part and a return cable part, than it is advantageous for avoiding of side bulging of the cable to dispose the feed cable part and the return cable part in each case such between two clamping blocks that they cross over. If the flat band with the thus disposed temperature-humidity measurement cable is placed annularly around a thermal insulation, then the cable parts bulge between the clamping blocks not toward the side, but continue to run substantially essentially in their pregiven longitudinal direction such that the temperature-humidity measurement cable passes assuredly into the region of the groove in the thermal insulation and not between its outer covering and the clamping band.

Advantageously, the flat band with the sensor cable is disposed in the region of a butt joint of the thermal insulation, which for example can be provided as a cassette insulation plate. Here the flat band covers a groove, which follows in the upper region of the thermal insulation to the butt joint. The measurement cable passes thus into the region of the groove, where the clamping straps with their side limiting webs run close to the side walls of the groove such that an assurance against a side shifting of the flat band is assured. The connection of the temperature-humidity measurement cable can be sealed in a connector block in the region of the receptacle, which is advantageously attached or, respectively, screwed in the region of a hole in the flat band. The connector block preferably comprises a humidity sealed and electrically insulating casting resin and is advantageously formed and disposed such that it is disposed in a plane with the clamping block or, respectively, the clamping straps in a longitudinal direction of the flat band and in addition in having the same width as the clamping strap such that upon solidly clamping of the flat band the connector block also centered engages into the groove and thus contributes to a securing against a possible side shifting.

A sealing strip can be disposed between the flat cable carrying the temperature-humidity measurement cable and the covering of the thermal insulation in order to achieve a further developed sealing closure. The sealing strip can run in the region of the longitudinal side walls of the flat band. The sealing strip can be made from an elastomeric, which can be provided as a more or less rigid foam with closed or also open cells. In addition, the sealing strip can be provided with adhesive on one or two sides for attachment of the flat type and/or to the covering. The groove in the region of the thermal insulation can have a substantially rectangular cross-section, where the adjoining butt position of the thermal insulation can be disposed as desired near the middle of the groove or also at one side. In addition, the base of the groove can be provided such that it runs substantially from the butt joint inclined outwardly in the direction to the side wall of the flat band, whereby in case of a leak the detection of the vapor part is favored exiting preferably from the butt joint. The inclined course of the base of the groove can be provided to the two sides substantially V-shaped. However, it is also possible to provide the groove base as a single inclined surface. In addition, the groove can be provided such that a step is furnished where the flat band is disposed substantially embedded or, respectively, sunk such that there is practically no protrusion outwardly at the circumference of the thermal insulation.

It is recommended for surveillance of a steam pipe or the like to provide several surveillance positions such that in case of a leak the leak in fact is recognized early and with certainty. It can be advantageous to feed several temperature-humidity measurement cables of the various surveillance positions to a subsidiary distributor box.

An electronic measurement value processing unit with measurement transducers for the temperature and humidity detection can be coordinated to the temperature-humidity measurement cable for the evaluation and surveillance. Advantageously, also a control computer system can be associated with such a measurement processing, which system as desired can comprise two microcomputers independent of each other for the temperature detection, for the humidity detection, for data collection, interference reporting and possibly a printer control. In addition, an alarm provision is furnished for detection purposes. It can be advantageous in an application in a power plant or the like to coordinate to the measurement value processing of the temperature-humidity cable a flow chart representation or also a picture screen display. These display apparatus can be advantageously installed in the control section of the power plant, which is substantially continuously operated by skilled personnel.

In addition, the invention temperature-humidity measurement cable can be applied or, respectively, disposed in a nuclear power station for detection of leaks in particular in a gully disposed in the floor of a room. Here the temperature-humidity measurement cable can be provided at an insertion body, which is disposed in a gully. It is recommended to dispose the sensor cable, located at the insertion body, immediately adjacent to a container wall of the fully such that also small amounts of liquid are monitored directly by the detection cable. Advantageously, the temperature-humidity measurement cable can be disposed in a circumferential recess of the insertion body for this purpose, and in fact such that the outer diameter in the region of the sensor cable is about equal or somewhat larger than the remaining diameter of the insertion body such that the detection cable is disposed substantially protected in the circumferential recess and nevertheless there exists a free access for the acceptance of the humidity. The temperature-humidity measurement cable can run in this case in several threads, preferably two to five windings, like a thread around the insertion body. A receptacle can be coordinated to the temperature-humidity measurement cable for receiving of a liquid sealing coupling plug of a test lead, where the receptacle is for example provided with four poles, where the start and the end of the sensor cable can be connected here. The receptacle advantageously is disposed here insulated in the insertion body such that a liquid sealing closure is provided in particular in the connection region of the detector cable. The receptacle and the insertion body with the integrated temperature-humidity measurement cable thus form a single compact building unit, which reliably meets the practical requirements during mounting and during later continuous operation. The receptacle can be supported according to one embodiment substantially in the middle region of the insertion body via radial support steadying struts. Large free spaces are provided between the support struts for the passage of a larger amount of liquid into the gully. The insertion body can be provided with a conical taper toward the bottom and can be provided at its upper end with a tiltable handling strap in particular for an easy removal from the gully. The insertion body can be from plastic, also stainless steel can be employed. The temperature-humidity measurement cable can run from the outer wall of the insertion body to the receptacle in the middle region under one of the radial support struts in their cross-sectional region along a corresponding recess such that in each case a protected support position is assured. According to another preferred embodiment the insertion body with the sensor cable can be disposed in a container part provided as a tube. This tubular container part can be attached to the inner surface of a ring insertable into the gully such that an off center disposition of the insertion body is provided. A trough-like feed for the liquid can be provided in the attachment region of the tubular container part at the ring through which a possible leakage liquid can be forcibly led into the tube container part and thus be guided to the temperature-humidity measurement cable disposed at the insertion body. The insertion body is supported substantially without play in the tubular container part. A liquid possibly flowing in from above can freely flow off at the bottom from the tube container part after passing of the sensor cable. The ring can be provided with a circumferential groove with an O-ring such that upon insertion into the gully a sealed closure is provided at the outer circumference of the ring and a possible liquid cannot pass by on the outside at the ring. Of course, also in case of this gully surveillance not only a change in humidity but also a change in temperature can be monitored such that also here two parameters for a sure and clear leak detection are used and detection is assured in case for example liquid exits from a container, a pipe system or the like and passes into the gully, where already small temperature changes between the leakage liquid and the room temperature are sensed.

Advantageously, a measurement value processing unit preferably with transducers, evaluation electronics, control system, printer, alarm provision and the like is coordinated to the gully surveillance with the temperature-humidity measurement cable according to the present invention. The gully supervision is particular important in those places which are normally not to be visited by human beings. These can be for example spaces in nuclear power stations, which based on a nuclear radiation danger are to be visited only in exceptional situations or after long intervals of time. A continuous remote surveillance is possible with the gully surveillance system of the present invention, which operates with high plant safety and provides a reliable permanent functioning and which operates without a potential such that external disturbing influences are excluded for practical purposes. The proposed gully system can in addition be produced and installed at a relatively low cost such that all gullies considered in the region of a power plant installation to be surveilled can be monitored without an inappropriately high cost expenditure, in particular, since after the installation of the gully surveillance system there are practically no current costs or these are reduced to a minimum.

It should be mentioned that the two temperature-humidity measurement cables in the humidity measuring part are fed to a humidity measuring part, which monitors a resistance change in the meg-ohm region between the wire conductor strands at the hygroscopic insulator. In addition, it is particularly advantageous if in case of need as desired such an electrical voltage can be applied to to the resistance wire of the temperature-humidity measurement cable that the resistance wire acts as an electrical heating element. By way of this invention step also a drying of possible humidity accumulations can be achieved with one and the same sensor cable, which for example can be advantageous for the performance of a control measurement in case of a preceding signal emission. Thus the possibility is provided to keep the detection system absolutely dry without additional means in order to assure reliable measurement performance. In addition, there is achieved practically a substantial economic advantage, since such a drying via the resistance wire acting as a heating element in the temperature-humidity measurement cable can release humidity or within a short time dry both the temperature-humidity measurement cable as well as its surroundings. Such a drying can be achieved already in a few minutes, while a drying otherwise without resistance wire heating can actually require several days.

The temperature-humidity measurement cable 101 shown in the drawing is part of a surveillance provision for the detection of leaks at containers or the like filled with liquids or vapor. It is provided as a multifunctional sensor cable formed as a unit and comprises two wire conductor strands 103, 104 acting as a conductor wire 102. The latter comprise thin individual copper wires which form a strand having a certain flexibility. The two wire conductor strands 103, 104 are in each case individually provided with a hydroscopic insulator 105, which is provided in the present embodiment as a woven glass filament tube covering. The two wire conductor strands 103, 104 as well as the hygroscopic insulator 105 are disposed in a wide insulator 106, which is also permeable to humidity and which is provided here as a tubular surrounding glass filament fabric. A resistance wire 107 is helically wound around the insulator 106 and serves to measure temperature, while the two wire conductor strands 103, 104 with the hygroscopic insulator are provided for humidity measurement, where the wire conductor strands 103, 104 are fed to a humidity measuring part, which monitors a resistance change in the megohm region between the wire conductor strands 103, 104. The temperature and the humidity are thus monitored with sensors in the detection cable of the invention, which sensors are completely separate from each other such that no mutual influencing can occur and potential-free results are obtained in each case.

The resistance wire 107, which belongs to a temperature measuring part, can if desired also be connected to such an electrical voltage (switching) that the resistance wire 107 operates as an electrical heating element. It is thereby in a simple way possible to eliminate rapidly possible humidity parts in the temperature-humidity measurement cable 101 and to remove them from the surroundings rapidly by drying. The temperature-humidity measurement cable 101 is provided on its outside with an outer jacket 108, which comprises a tube shaped covering glass filament fabric and which surrounds the previously mentioned wire conductor strands 103, 104 their hygroscopic insulator 105, the insulator 106 and the resistance wire 107. A feedback conductor 109 is disposed at the outer jacket 108, which is fixed with corresponding electrical support rings or the like at the outer jacket 108. The return conductor 109 is provided on its outside with a temperature resistance Teflon insulation 110, where also silicone caoutchouc and glass filament can be provided. The return conductor 109 can be connected by way of a soldering or welding connection with the end of the resistance wire 107 at for example in case of a non-returned temperature-humidity measurement cable 101 as a return line.

Figure 2:
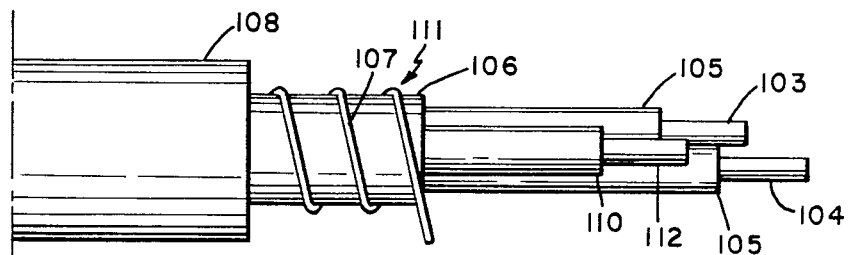
FIG. 2 is a side elevational view of a further embodiment of a temperature-humidity measurement cable similar to that of FIG. 1.
Figure 3:
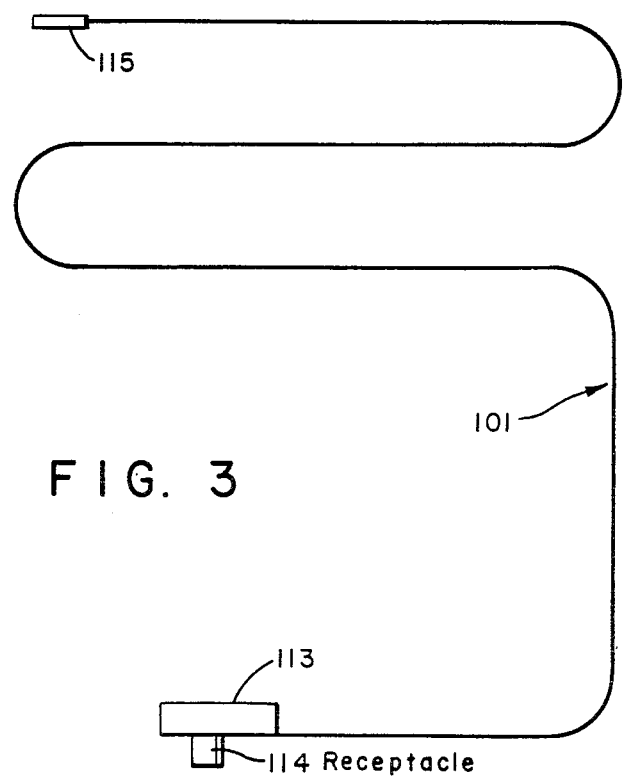
FIG. 3 is a total view of a free running temperature-humidity measurement cable.
Figure 7:
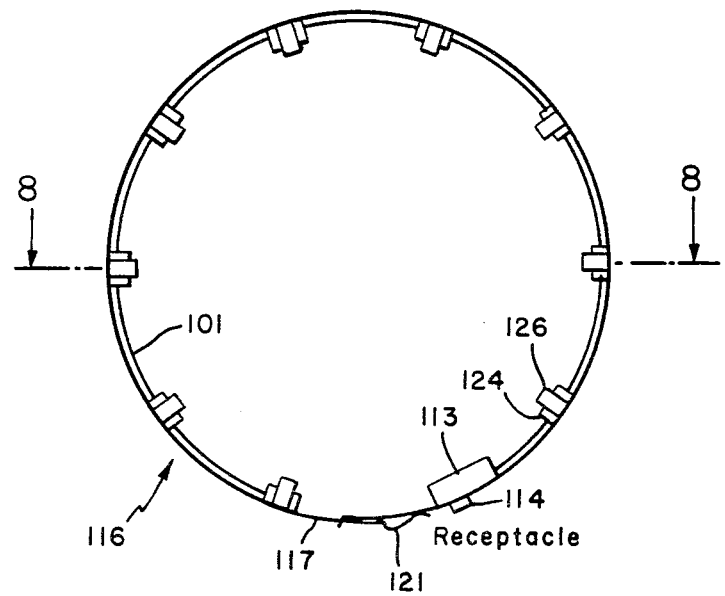
FIG. 7 is a view of the detection band according to FIGS. 4 to 6 in a circular curved representation as employed when mounting around an insulated steam pipe or the like, FIG. 8 is a sectional view of the detection band according to FIG. 7.
Figure 8:
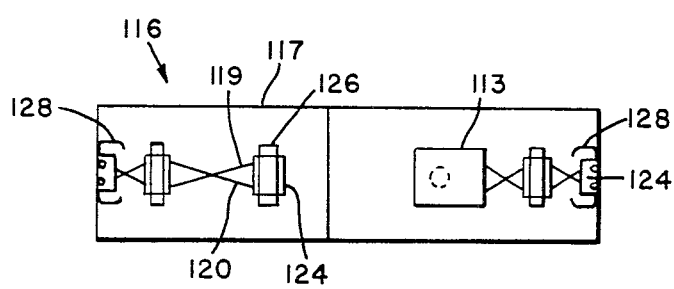

The temperature-humidity measurement cable 111 shown in FIG. 2 is provided substantially as the temperature-humidity measurement cable 101. Therefore, the corresponding parts are designated with corresponding numerals. The substantial difference comprises that the return conductor 112 runs parallel to the wire conductor strands 103, 104 within the tubular surrounding insulator 106. It is further within the framework of the invention to provide the return line 112 for example as a braided copper material under the insulator 106.

The temperature-humidity-measurement cable 101, 111 can be installed substantially free and without any particular restrictions such that a desired arrangement can be furnished along a pipe line having preferably a stuffed insulation.

The temperature-humidity measurement cable 101 is provided at one end with a connector block 113 with a multiple pole electrical receptacle 114. This is supported in the electrical connector block 113 under humidity and electrical insulation, since the connector block 113 is provided from a corresponding casting resin, which is preferably temperature stable and elastic. The temperature-humidity measurement cable 101 is provided at its other end end with a base load resistor 115, which is disposed between the wire conductor strands 103, 104 and which in addition can be used for a monitoring of a rupturing of a wire.

The detector tightening strap 116 illustrated in the FIGS. 4 to 11 has the temperature-humidity measurement cable 101 provided as a cable winding 118 attached to a flat band 117, which winding is provided with a feed cable part 119 and a return cable part 120. The flat band can comprise about 1.5 millimeter thick stainless steel sheet, which has a toggle type fastening connector 121 operated by a tilting lever and disposed at the one end for a rapid connection, which can be fine step adjusted for a tolerance balancing and which engages at the other end region of the flat band 117 into a counterpiece 122. The temperature-humidity measurement cable 101 is supported in the longitudinal grooves of several clamp blocks 124 with its feed cable part 119 and its return cable part 120. The clamping blocks 124 are attached at essentially equal distances of about 50 centimeters at the flat band 117 and they are provided from silicone caoutchouc according to a preferred embodiment, which in addition to a good electrical insulating property also exhibits a permanent temperature stability. An insulating foil 125, comprising for example a polyimide film such as the films supplied by DuPont de Nemours under the trademark of Kapton, which are preferably from about 25 to 125 microns thick, such that also a high value insulation is provided between the temperature-humidity measurement cable 101 and the flat band 117 for shielding against external interfering influences for such a potential-free performance of the measurement. The clamping blocks 124 are in each case attached to a clamping strap 126, which is demountably attached to the flat band 117 by way of screws. Each clamping strap 126 is provided on the two sides of the flat band 117 with outward border webs 128, the free ends of which are rounded into arc-shape. It can be further recognized that the feed cable part 119 and the return cable part 120 in each case run such in the region between two clamping blocks 124 that they cross over. Thereby in case of a round bending of the flat band 117 into a circle it is avoided that the feed cable part 119 and the return cable part 120 bent off outwardly in an arc. It can also be recognized that the width of the connecting block 113 essentially is equal to the width of the clamping straps 126 and is disposed in the same middle plane as seen in the longitudinal direction with the clamping straps 126. A cross groove is formed in the clamping block 124 disposed remote from the connector block 113 between the longitudinal grooves 123, wherein the redirection of the temperature-humidity measurement cable 101 is provided.

Figure 9:
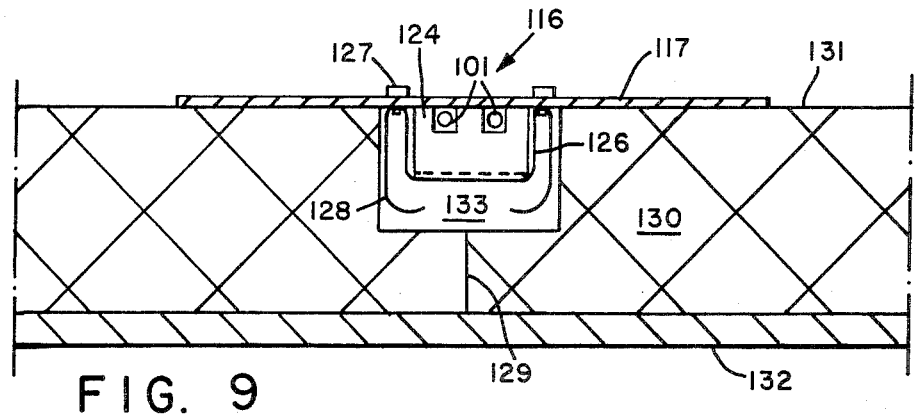
FIG. 9 is a partial sectional view of an insulated steam pipe with a detection band according to FIGS. 4 to 8.
Figure 10:
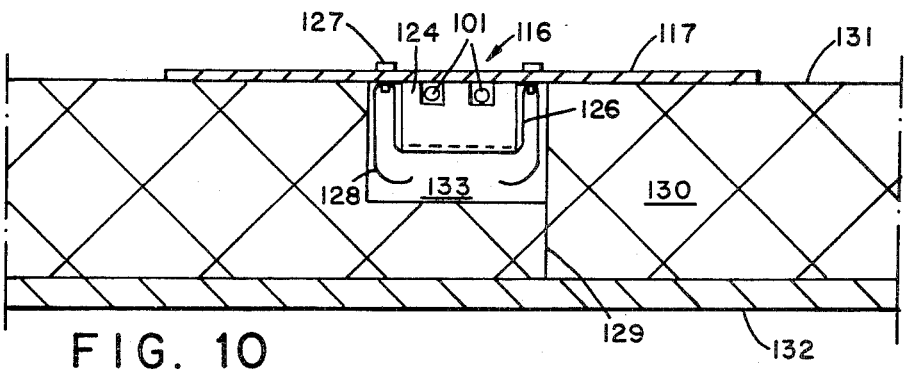
FIG. 10 is another partial sectional view of an insulated steam pipe similar to that of FIG. 9.
Figure 11:
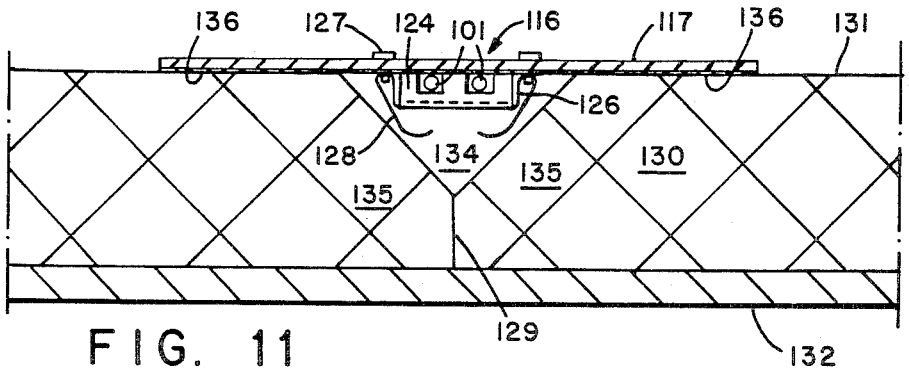
FIG. 11 is a further partial sectional view of a stem pipe similar to FIGS. 9 and 10.

It can be recognized from the FIGS. 9 to 11 that the temperature-humidity measurement cable 101 is disposed substantially in the region of the butt connection 129 of joined thermal insulation pieces 130 and substantially within the plane of the outer covering 131. The thermal insulation 130 surrounds the wall 132 of a steam tube. The butt connection 129 is disposed in the middle of the base of the rectangular groove 133 according to the embodiment of FIG. 9. The butt connection 129 is again in the middle of the groove 133 according to FIG. 10, while FIG. 11 shows the butt connection 129 again joining in the middle of the groove 134, which is here substantially formed as a triangle such that inclined parts 135 are present. In addition, a sealing strip 136 is provided here between the flat band 117 and the covering 131 of the thermal insulation 130 at the two sides of the flat band. The clamping strap 126 is provided such with its two side bordering webs 128 that the latter engage the groove 133, 134 approximately matching and they position the detection tightening band 116 during mounting and beyond safely against a shifting to one or the other side. The advantage of production under favorable cost conditions in the production of the thermal insulation 130 can be achieved by the provision of the inclined parts 135. It is within the range of the invention to provide the thermal insulation or respectively the groove such that the base of the groove is formed exclusively by a single inclined part, while the other groove limitation is formed by the butt connection 129 extending to the outer covering 131. Also in this case a cost favorable production can be achieved.

Figure 12:
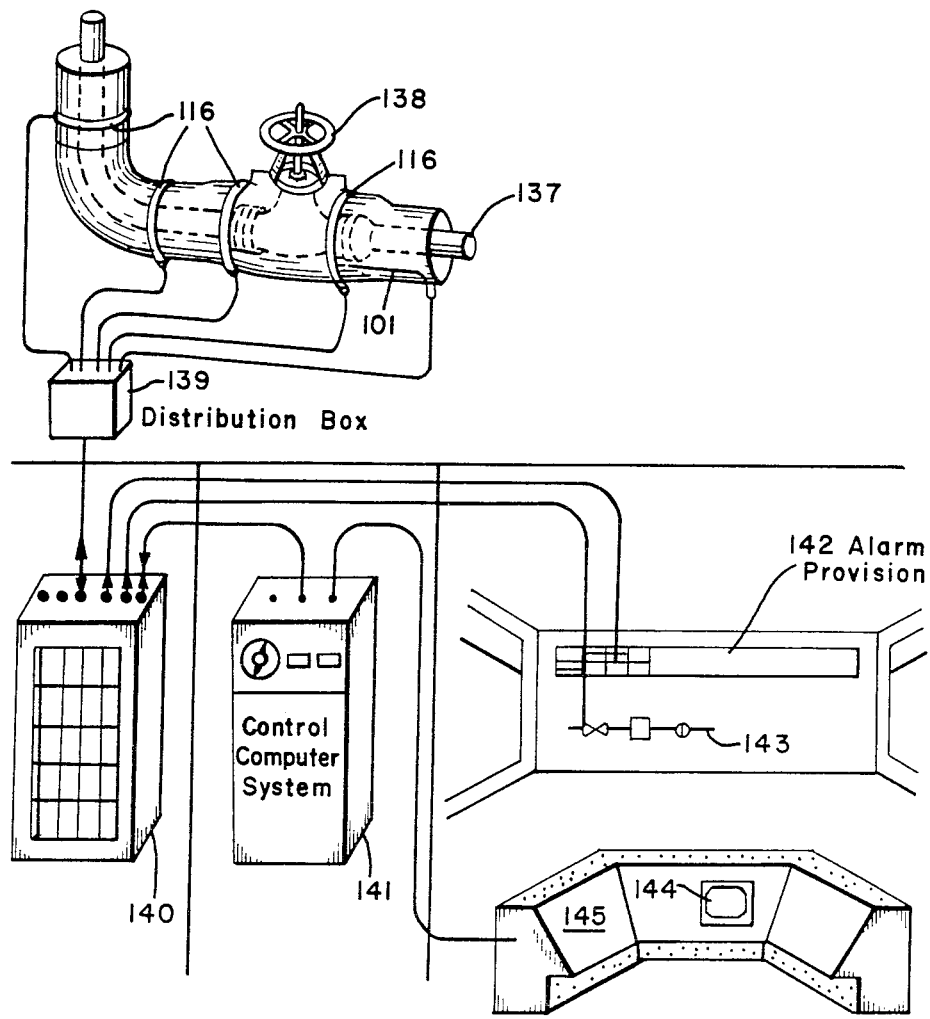
FIG. 12 is a schematic view of a surveillance system for leakage detection.

A surveillance provision with five measurement locations is shown in FIG. 12, of which four measurement positions are formed by detection tightening straps 116, which are disposed at the butt connections of a thermal insulation 130 of a steam pipe 137, where two detection tightening bands 116 are disposed in the area of the connection flanges of the valve 138. A measurement position is provided as a free sensor cable installed in parallel to the longitudinal direction of the steam pipe 137 in the region of the thermal insulation 130. Measurement lines run from five temperature/humidity sensors 101 or, respectively, 116 disposed at the steam pipe 137 to a subsidiary distribution box 139, where this group of sensors is initially combined.

A connection is provided from here to an electronic measurement value processing unit 140, which measurement value processor and a control computer system 141 are coordinated with two microcomputers to data collection, interference reporting, measurement evaluation, printing, and to temperature and humidity determination. The microcomputers operate independently from each other. In addition, an alarm provision 142 is coordinated to the measurement value processing 140 in a control room of a nuclear power plant and in addition a flow chart representation 143 as well as a picture screen representation are provided for continuous control with inquiries as desired. The measurement results can be fixed on paper by a printer 145.

Figure 13:
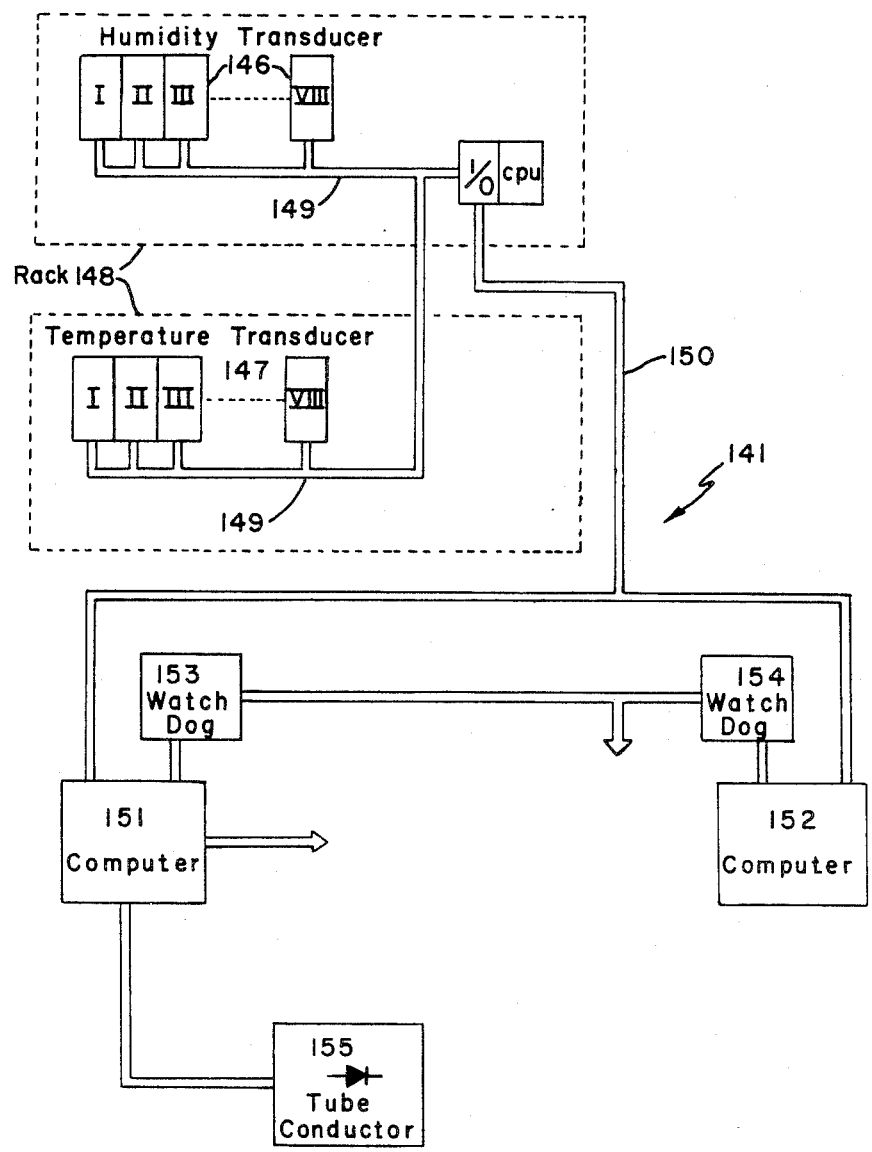
FIG. 13 is a schematic view of an invention surveillance system for leakage detection with a computer evaluation part.

The construction with the computer evaluation with the humidity measurement transducer 147 as well as the control computer system 141 are shown in FIG. 13. A substantial importance is associated here with the plant safety and with the overviewability. All computers and transducers employed are produced according to the C-Mos technique. This assures a low current use and a large interference distance. The connections within a 19 inch rack 148 are combined onto a large wiring board (backplane) 149. The insertion frame comprises eight humidity transducers 146, eight temperature transducers 147, a microcomputer for the surveillance and cyclical functioning checking of the sixteen transducers as well as a data processing unit for serial, bidirectional transfer onto a two wire data bus 150. The control computer system 141 is provided completely redundantly. Up to 1024 transducers can be connected via a bidirectional two wire data bus. The control computer system 141 is provided with two microcomputers independent from each other (100 percent redundant) for data collection, interference reporting, printer control and the like. The outputs of the computer 151 run to the printer, the keyboard, the collection report, the display absolute value and the display number of the test location. A so-called "watch dog" 153, 154 is provided for switching over in case of a failure of one of the computers 151, 152 and between them there is provided an output to a system disturbance or, respectively, system disturbance display. The computer 151 is connected to a tube conductor constructions 155. An alphanumeric printer is employed for documentation of all reports, questioning, disturbances and the like. A sixteen field keyboard is provided in order to be able to select up to a 1000 measurement points. In addition, two display fields with each two four position seven segment displays can be employed and a control circuit can be provided for controlling a display table with up to 1000 light emitting diodes. However, it is within the range of the invention to provide or to adapt the control system 141 also in another or, respectively, smaller embodiment, where in particular an integration into already available surveillance provisions can be considered in case of a supplementary installation of the surveillance system of the invention.

The central unit with two independent computers in parallel disposition and mutual consistency control performs in a measurement processing procedure the following most important functions: Control of the test cycles, surveillance of the subcomputers, surveillance of the data bus, control of printer and displays, keyboard input, selfinspection, selftesting. The system offers the following possibilities for selecting measurement points and signalling, which can be in operation simultaneously: signalling of the limiting value outputs optically, acoustically and printer output; manual selection of a test location for observing trends, where the measurement value is displayed continuously together with the number of the test measurement location; analog output for plotters, where desired measurement locations can be switched on via the input keyboard to various outputs.

The test program comprises the following possibilities: Remote control of the test line with regard to possible ruputre or short circuit of the test head for example by external application of force; cyclical performance of tests; monitoring of test programs of all transducer functions and limiting signal processing; group composition of the transducers and checking by independent subcomputers; retaining of possible defective signals or test errors in the processing of measurement values in case of a possible transducer or computer failure.

Figure 14:
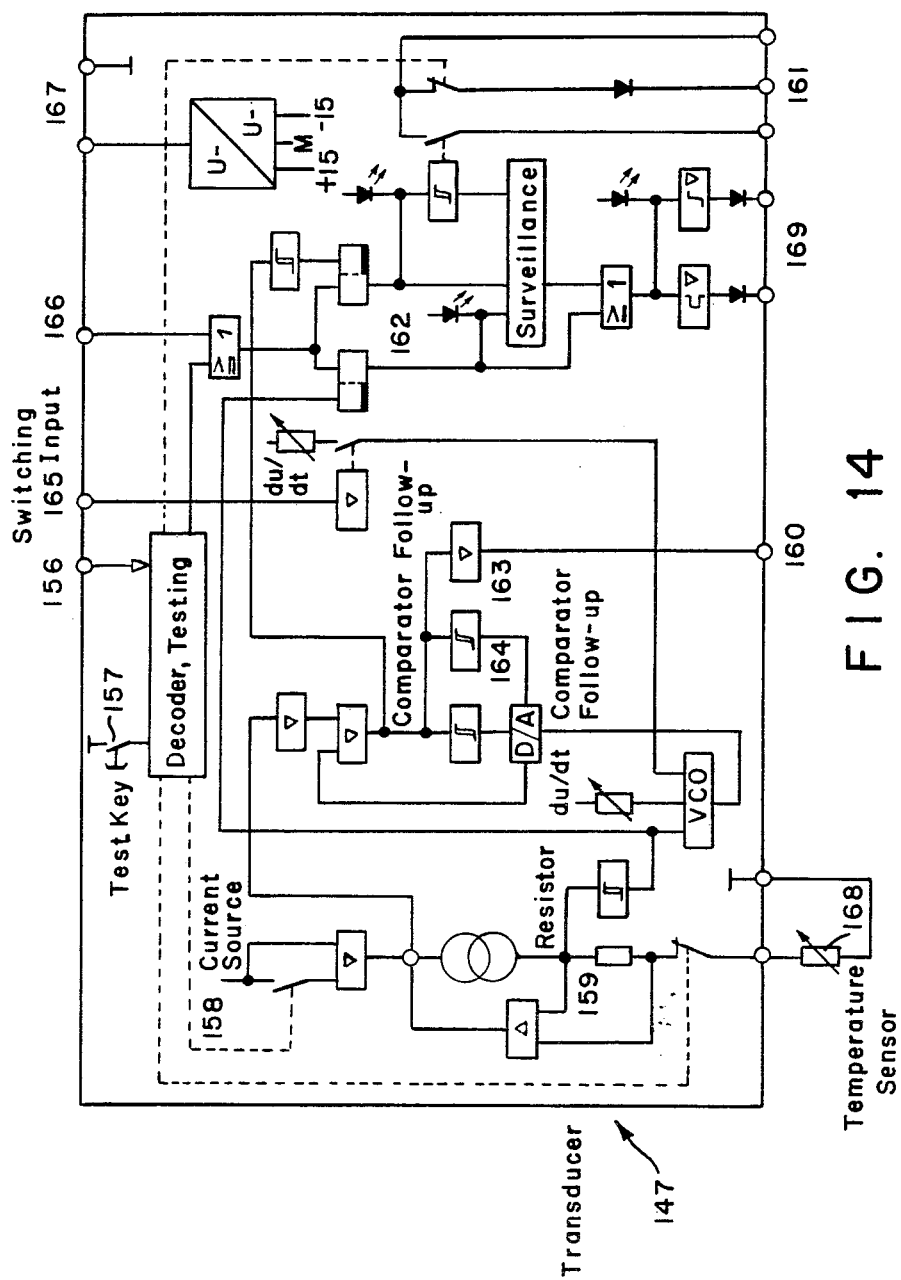
FIG. 14 is a representation of a temperature-transducer of the surveillance station for leakage detection.

The temperature measurement transducer 147 shown in FIG. 14 is provided with the following functions: Amplifier testing 156 as well as testing of the measurement value processing and test head breakage, test key 157 for manual testing, set point constant current source 158, range determining resistor 159, switchable, analog output 160, limiting value output 161, potential free and display on a front plate, test head breakage indicator 162 on the front plate, comparator follow-up 163 (stop), comparator follow-up 164 (higher-lower), gradient switching input 165, acknowledgement 166, 24 volt input 167, temperature sensor 168 and measurement interference display 169. The technical data of the temperature transducer 147 at the present embodiment comprise a range of 100 to 1000 ohm, a maximum measurement span plus/minus 200 ohm and a maximum operating range equalization control plus/minus 200 ohm. An automatic null balancing of the transducer is provided after the taking into operation or elimination of a possible interruption of the test breakage signal. The balancing control compensates possible resistance changes in the line to the test head. The maximum setting of the measurement span "Dynamic change" comprise plus/minus 200 ohm, while the maximum settable measurement span "Dynamic change" amounts to plus/minus 5 ohm. In addition, a switching over du/dt (stationary operation/start-up operation) is provided, where the settability of du/dt is possible between 1 V/h and 1 V/sec.

Figure 15:
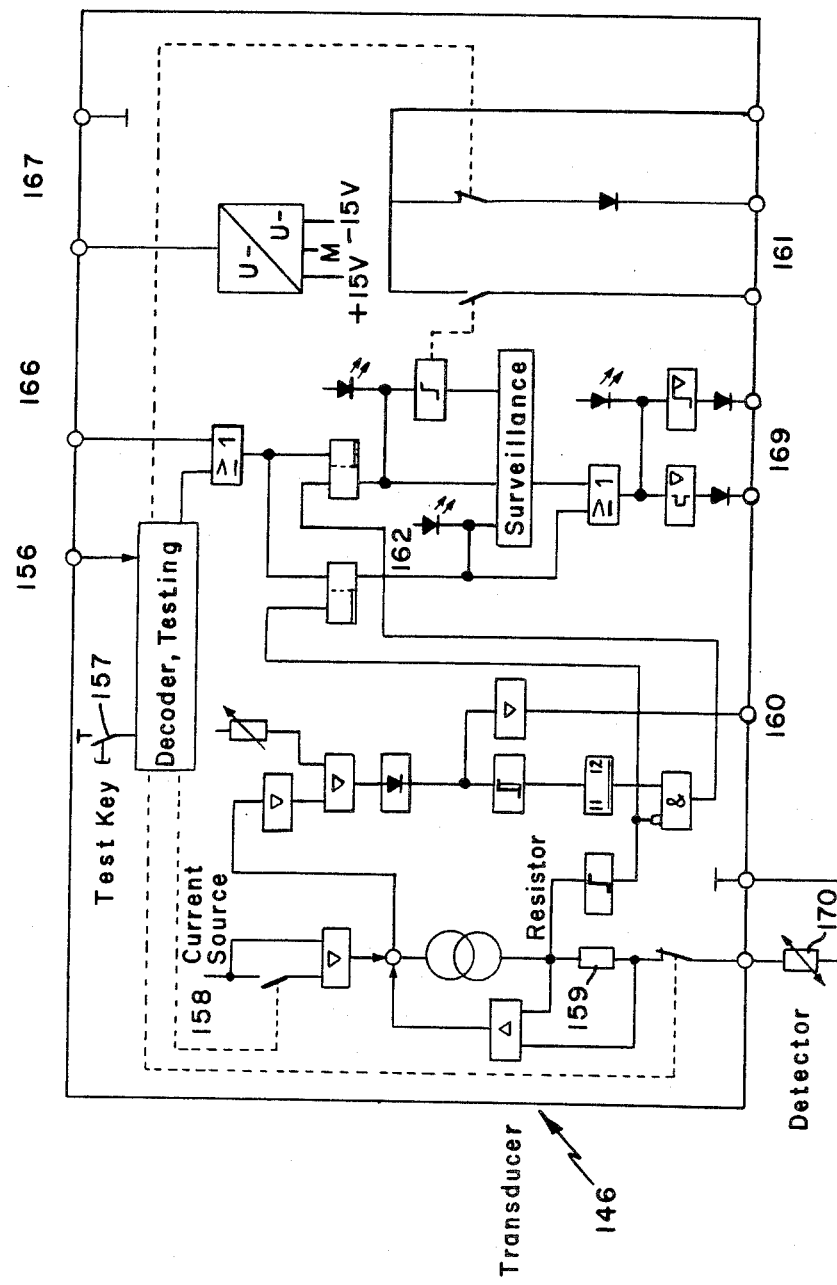
FIG. 15 is a representation of a humidity transducer of the surveillance station for leakage detection.

The humidity transducer 146 shown in FIG. 15 also comprises an amplifier testing 156, which also serves to test the measurement processing and a for breakage of the test head. In addition, a test key 157 for manual testing and a set point constant current source 158 as well as a switchable measurement range resistor 149 can be provided. Furthermore, an analog output 160, a limiting value output 161 (free from potential and display on the front plate), an acknowledgement 166, a 24 volt input 167 as well as a measurement interference indication 169 and a humidity detector 170 can be recognized. The technical data of the humidity transformer 146 are as follows: measurement range 0 to 200 K-ohm, 0 to 2 megohm, 0 to 10 megohm (0 to 10 V), falling characteristic curve. The limiting value output voltage is larger than 0.5 volts. The base load resistance 220 K-ohm, 2.2 megohm, 12 megohm. The response speed is smaller than 1 second at a measuring range of 10 megohm, the resistance is smaller than 9.8 megohm. The noise suppression is larger than 70 dB at 50 hertz. The maximum length of the line amounts to about 3000 meters.

Figure 16:
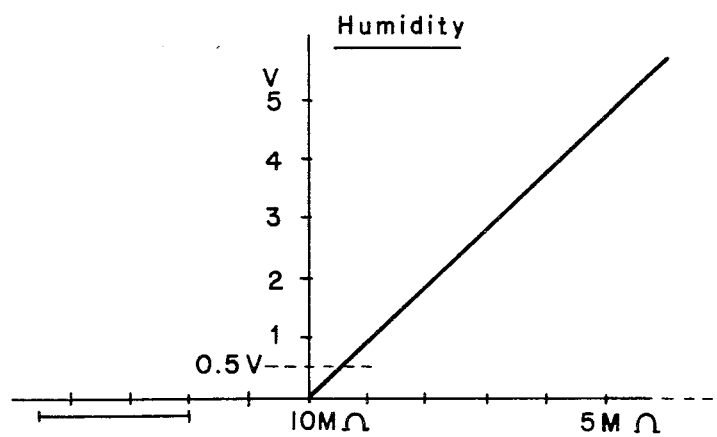
FIG. 16 is a diagram showing an example of setting the humidity transducer.
Figure 17:
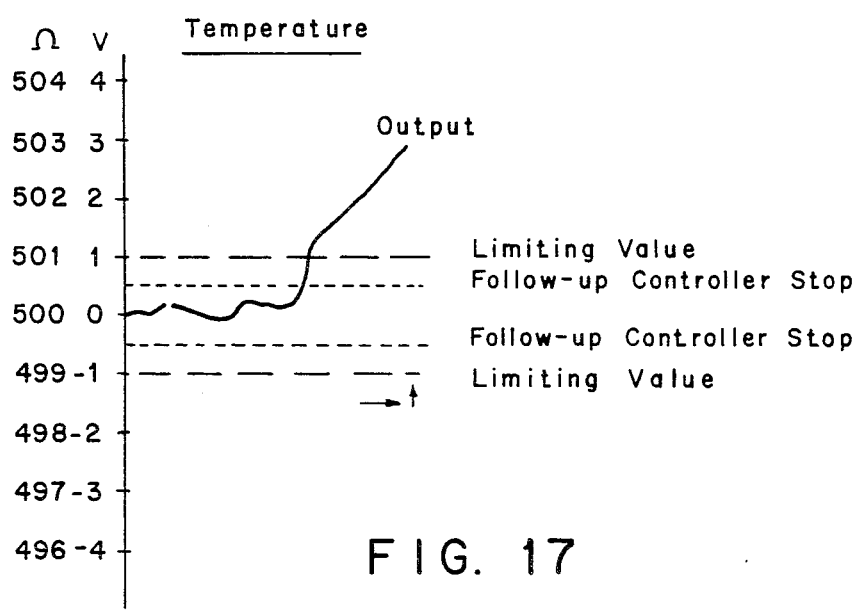
FIG. 17 is a diagram showing an example of setting the temperature transducer.

The FIGS. 16 and 17 show examples of settings for the humidity transducer 146 and, respectively, for the temperature transducer 147.

Figure 18:
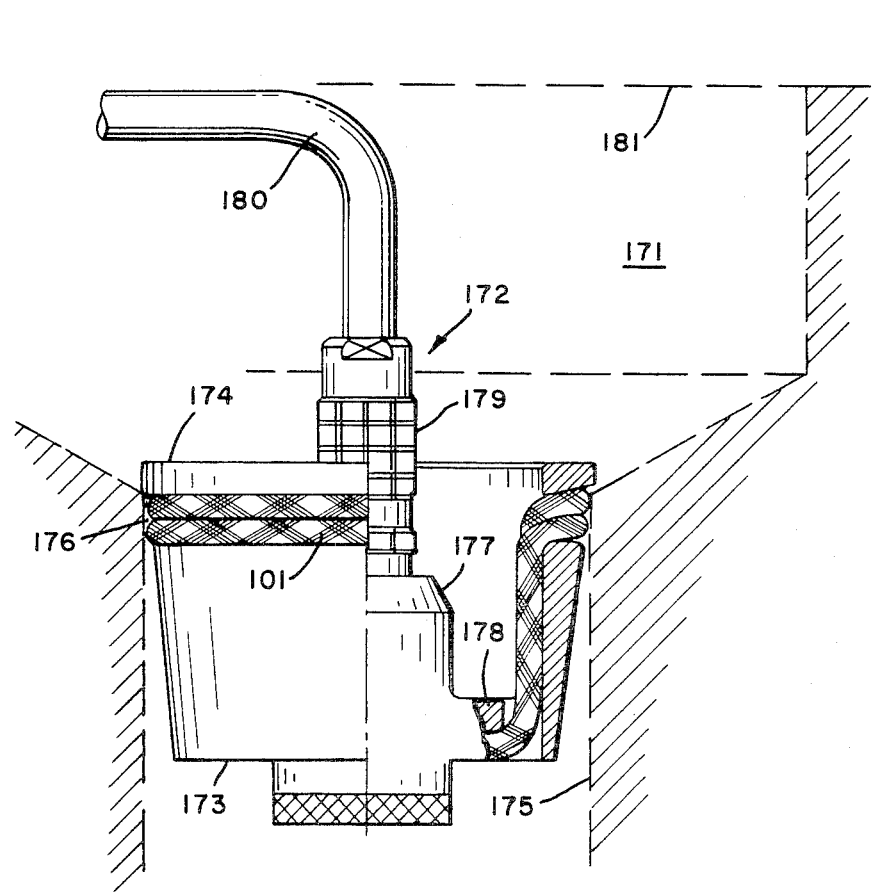
FIG. 18 is a partially sectional view of a gully detector of the invention surveillance provision with a temperature-humidity measurement cable.

A gully detector 172 is shown in a gully 171 in FIG. 18. The gully can be located in the floor of a nuclear power station room. In case of an inflow into the gully 171 of water exiting from a leak corresponding signals are released within the frame of the surveillance provision. The temperature-humidity measurement cable 101 is disposed at an insertion body 173, which is located within the range of the gully. The insertion body 173 comprises a suitable plastic material and is conically tapered toward the bottom according to the present embodiment. The insertion body 173 is on top provided with a slightly larger circumferential rim 174, which rests on top of the container wall 175. A circumferential recess 176 is provided in the insertion body 173 immediately below the circumferential rim 174 and the temperature-humidity measurement cable 101 is disposed in the circumferential recess 176. A receptacle 177 is sealing against humidity and is disposed in the middle of the insertion body 173. The receptacle is supported by two radial supporting struts 178. Free spaces are provided between the support struts 178 in the insertion body 173 such that the insertion body is substantially open for the flow through of possibly larger amounts of water. The sensor cable 101 is led from the receptacle 177 through the support strut 178 upwardly into the region of the circumferential recess 176, wherein it rests fitting with two circumferential windings. The sensor cable 101 is then again fed back through the support strut 178 to the receptacle 177. The disposition of the sensor cable 101 is arranged such that the diameter is slightly larger in the area of the two sensor cable windings as compared to the diameter of the insertion body 173 below. In addition, the diameter in the range of the sensor cable windings is such adjusted to the diameter of the container wall 175 that the temperature-humidity measurement cable 101 is disposed closely spaced to the container wall 175 such that in case of an only small feeding of water immediately and necessarily a reception by the temperature-humidity measurement cable 101 occurs, where not only a signal regarding the presence of humidity is provided, but also a signal is provided via the temperature display, if the entering leakage water for example has a somewhat different temperature as the temperature of the environment. A plug 179 of a corresponding four pole measurement line 180 is sealing against liquid passage and inserted into the receptacle 177, however it is nevertheless at any time disconnectable and reconnectable. The measurement line 180 runs under the gully cover 181 to the edge region of the gully 171 and is fed from here to the measurement processing.

Figure 19:
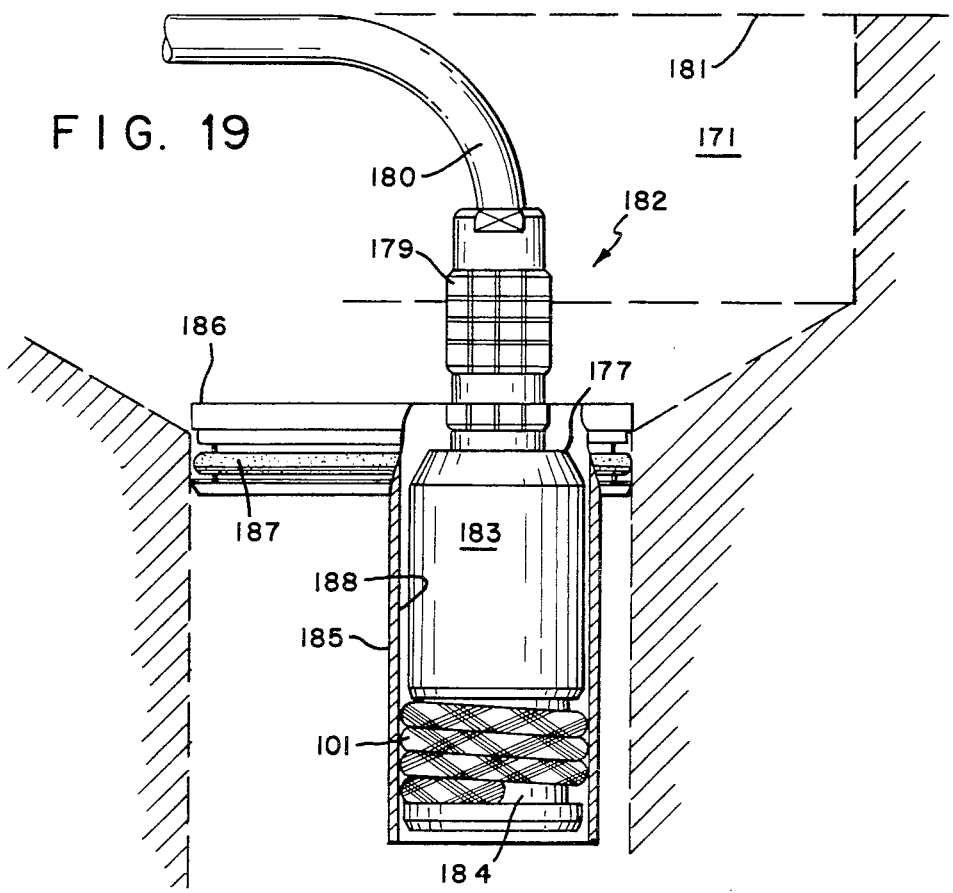
FIG. 19 is a view, partially in section, of a gully detector of a surveillance unit.

The gully detector 182 shown in FIG. 19 is also inserted into a gully 171, which is covered with a gully cover 181. The gully detector 182 comprises also a measurement line 180 with a plug 179, which is inserted into the receptacle 177 of an insertion body 183 sealing against passage of liquids. The receptacle 177 is absolutely sealingly disposed at the insertion body 183. The temperature-humidity measurement cable 101 runs from the receptacle 177 in the interior of the insertion body 183 outwardly and is here fittingly disposed in preferably four windings in a circumferential recess 184 of the insertion body 183 and is returned back from here to the receptacle 177.

The insertion body 183, which is provided as the previously described insertion body 173 with the receptacle 177 and the temperature-humidity measurement cable 101 as a substantially single piece and easily manipulatable construction unit, is disposed in a tubular formed container part 185, which is attached to the inner side edge off center in the range of the ring 186. The ring 186 is provided with an O-ring 187 positioned in a circumferential groove and the O-ring contacts the gully wall sealingly. A trough-shaped liquid feed is provided in the area of the attachment of the container part 185 at the ring 186 such that possible leakage water is forcibly led initially to this location into the container part 185, where an immediate signal is provided via a humidity measurement part and/or via the temperature measurement part based on the practically play free disposition of the temperature-humidity measurement cable 101 in the region of the container wall 188.

Figure 20:
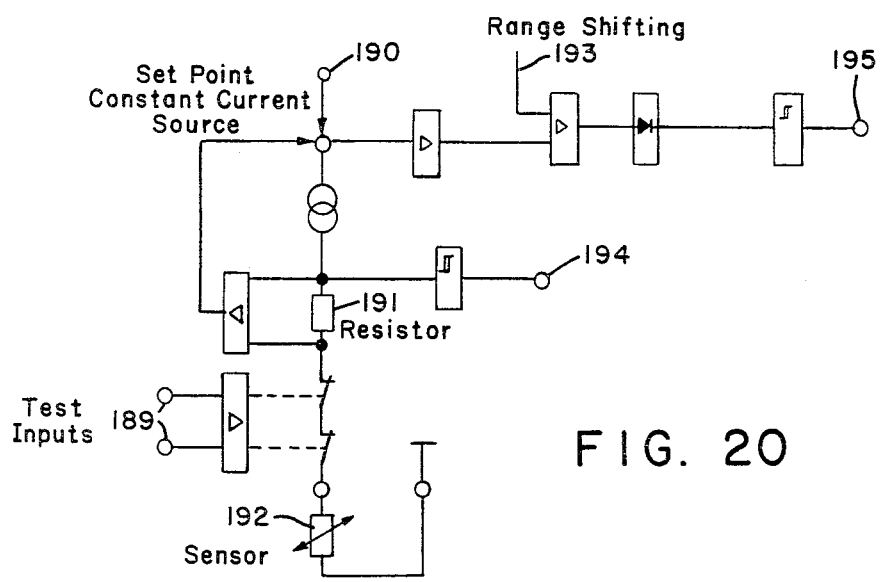
FIG. 20 is a schematic representation of the surveillance unit for leakage detection with gully surveillance.

A schematic diagram relating to the gully surveillance according to the invention is shown in FIG. 20 with the following functions: test inputs 189, set point constant current source 190, measurement range resistor 191, humidity/temperature sensor 192, range shifting 193 for the base load resistor, test head breakage output and limiting value output 195.

The monitoring of the measurement values of the gully surveillance provision comprises thus just as the steam pipe surveillance provision a humidity detector with integrated temperature sensor, where the temperature sensor provided as a resistance wire can also be employed as a heating element for the sensor cable drying in the range of the gully detector upon proper voltage feeding. The detection system is absolutely free of potentials. The humidity detector comprises the copper wires with variable base load resistance for the sensitivity and wire rupture surveillance. The insulations comprise several layers of wound glass filament fabric. All measurement cables usually employed in the MSR-technique can be connected. The maximum line length is about 3000 meters. Depending on the test head base resistor measurement regions of between 1 and 20 megohm can be set. The limit output voltage is preferably larger than 200 millivolt. The response speed is smaller than 1 second at a measuring range of 10 megohm-0. The noise suppression is larger than 70 dB at 50 hertz. The measurement value processing is performed essentially advantageously as set forth in connection with the above described steam pipe surveillance and can comprise transducers, an evaluation electronic circuitry, control systems, alarm provisions and the like.

The invention sensor cable 101, 111 can be employed particularly advantageously in the framework of the present invention also at noninsulated pipes, at containers, or the like in order to monitor possible temperature and/or humidity changes. It is possible in this context to position the temperature-humidity measurement cable 101, 111 for example coaxially on the outside at a tube wall and to attach it by way of support straps, bands or the like. Also, the measurement cable 101, 111 can be wound spirally around the tube or, respectively, the object to be monitored such as a valve, a pressure balancing aggregate, a manometer, or the like.

It will be understood that each of the elements described above, or two or more together, may also find a useful application in other types of surveillance and monitoring system configurations and fluid and nuclear processing procedures differing from the types described above.

While the invention has been illustrated and described as embodied in the context of surveillance equipment for liquid containers and nuclear power plants, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. A measurement cable surveillance provision for pipe-like containers of fluids for continuous temperature and humidity sensing comprising
   a first electrical conductor wire;
   a second electrical condutor wire running substantially parallel to the first electrical conductor wire and where the first and the second conductor wire are substantially similar;
   a hygroscopic insulator means disposed between the first and the second electrical conductor wires for providing humidity control and for spacing said conductor wires at a predetermined distance relative to each other;
   a humidity permeable insulator surrounding the hygroscopic insulating means and the first and second electrical conductor wires;
   a helically disposed resistance wire for temperature sensing purposes running on the outside of the humidity permeable insulator and about along the electrical conductor wires and disposed at a spaced distance from the first and the second electrical conductor wires.

2. The surveillance provision for containers of fluids according to claim 1 wherein the containers are steam pipes.

3. The surveillance provision for containers of fluids according to claim 1 wherein the hygroscopic insulating means depends on humidity and wherein the electrical conductor wires, the hygroscopic insulating means, and the resistance wire are provided as a multifunctional temperature-humidity test cable.

4. The surveillance provision for containers of fluids according to claim 3 wherein the electrical conductor wires are provided as stranded wires made from thin individual wires.

5. The surveillance provision for containers of fluids according to claim 3 wherein the hygroscopic insulator means of the temperature-humidity cable is provided as a jacket surrounding at least one of the electrical conducting wires.

6. The surveillance provision for containers of fluids according to claim 3 wherein the hygroscopic insulating means comprises glass filament insulation.

7. The surveillance provision for containers of fluids according to claim 3 wherein the hygroscopic insulating means is provided as a woven, braided glass filament tube surrounding at least one of the electrical conductor wires.

8. The surveillance provision for containers of fluids according to claim 3 where the electrical conductor wires are strands of thin wires.

9. The surveillance provision for containers of fluids according to claim 8 wherein the permeable insulator surrounding the electrical conductor wires and the hygroscopic insulating means is a fabric tube formed from glass filaments.

10. The surveillance provision for containers of fluids according to claim 8 wherein the resistance wire of the temperature-humidity measurement cable is disposed spirally around the insulator surrounding the stranded wires of the electrical conductor wires and the hygroscopic insulating means.

11. The surveillance provision for containers of fluids according to claim 8 further comprising a humidity permeable outer jacket surrounding the two electrical conductor wires and the hygroscopic insulating means disposed in the permeable insulator and the resistance wire.

12. The surveillance provision for containers of fluids according to claim 11 wherein the outer jacket of the temperature-humidity measurement cable is provided as a braided glass filament tube.

13. The surveillance provision for containers of fluids according to claim 11 further comprising a return line coordinated to the resistance wire for temperature sensing in a temperature measurement, which is connected to the end of the resistance wire with a fused metal connection and which is insulated so as to be temperature stable.

14. The surveillance provision for containers of fluids according to claim 13 wherein the return line is disposed on the outside of the temperature-humidity measurement cable and where the insulation of the return line is provided by a member of the group consisting of tetrafluoroethylene, glass filaments, and mixtures thereof.

15. The surveillance provision for containers of fluids according to claim 13 wherein the return line of the resistance wire is provided by a stranded copper wire disposed inside of the outer jacket and running substantially in parallel to the electrical conductor wire strands.

16. The surveillance provision for containers of fluids according to claim 13 wherein the return line of the resistance wire is provided substantially as a braided cover.

17. The surveillance provision for containers of fluids according to claim 13 further comprising
a base load resistor coordinated to the electrical conductor wires of the temperature-humidity measurement cable for humidity detection and/or rupture surveillance.

18. The surveillance provision for containers of fluids according to claim 17 wherein the base load resistor is disposed between the two stranded electrical wire conductors at the end opposite to the connection point of the temperature-humidity measurement cable.

19. The surveillance provision for containers of fluids acording to claim 3 wherein the temperature-humidity measurement cable is provided with a connector part provided as a multipole receptacle.

20. The surveillance provision for containers of fluids according to claim 3 wherein the temperature-humidity cable is disposed substantially free in the region of a stuffed solid insulation between the wall of a steam pipe and an outer covering in the longitudinal direction and/or surface direction of the steam pipe.

21. The surveillance provision for containers of fluids according to claim 3 further comprising
a flat band supporting the temperature-measurement cable.

22. The surveillance provision for containers of fluids according to claim 21 wherein the flat band is provided with a toggle type fastening clamp adjustable in small steps.

23. The surveillance provision for containers of fluids according to claim 21 wherein the temperature-humidity cable is fixed in a desired position via a clamping block attached to the flat band.

24. The surveillance provision for containers of fluids according to claim 23 wherein the temperature-humidity cable is guided by at least one longitudinal groove of the clamping block.

25. The surveillance provision for containers of fluids according to claim 21 wherein the temperature-humidity measurement cable is disposed with a feed cable part and a return cable as a cable loop at the flat band.

26. The surveillance provision for containers of fluids according to claim 23 wherein the clamping block has two substantially parallel longitudinal grooves for receiving the feed cable and the return cable.

27. The surveillance provision for containers of fluids according to claim 23 wherein the clamping block comprises an elastic and temperature resistant insulating material.

28. The surveillance provision for containers of fluids according to claim 23 wherein the clamping block comprises silicon caoutchouc.

29. The surveillance provision for containers of fluids according to claim 23 wherein an insulating foil is disposed at least in the region of the clamping block between the temperature-humidity measurement cable and the flat band.

30. The surveillance provision for containers of fluids according to claim 23 wherein the clamping block is fixed with a clamp strap at the flat band.

31. The surveillance provision for containers of fluids according to claim 23 wherein the temperature-humidity measurement cable is attached to the flat band by way of several clamping blocks disposed at a distance in longitudinal direction and where the feed cable and the return cable run crossing over between two clamping blocks.

32. The surveillance provision for containers of fluids according to claim 23 further comprising
a connector block from cast resin shielding against humidity and insulating electrically, which seals the temperature-humidity measurement cable in the region of the receptacle.

33. The surveillance provision for containers of fluids according to claim 23 wherein the connector block is disposed in the longitudinal direction of the flat band substantially within a plane with the clamping block or, respectively, clamping strap and has about the same width as the clamping strap.

34. The surveillance provision for containers of fluids according to claim 23 wherein the temperature-humidity measurement cable is disposed at the region of a butt connection of the thermal insulation, where the flat band covers the groove adjoining the butt connection and where the flat band is secured in the groove by way of side limiting webs of the engaging clamping straps against a sideways shift.

35. The surveillance provision for containers of fluids according to claim 23 further comprising
a sealing strip provided between the flat band supporting the temperature-humidity cable and the covering of the thermal insulation.

36. The surveillance provision for containers of fluids according to claim 23 wherein the bordering wall of the groove is provided with at least one inclined part extending essentially from the bottom of the groove in the region of the butt connection of the thermal insulation.

37. The surveillance provision for containers of fluids according to claim 3 further comprising
a subsidiary distributing box connected to the temperature-humidity measurement cables of different surveillance positions.

38. The surveillance provision for containers of fluids according to claim 3 further comprising
an electronic measurement value processing unit including measurement transformers for evaluating and monitoring of temperature and humidity.

39. The surveillance provision for containers of fluids according to claim 38 further comprising
a control computer system coordinated to the measurement processing unit connected to the temperature-humidity measurement cable which comprises two independent microcomputers for providing data collection, interference reporting and printer control.

40. The surveillance provision for containers of fluids according to claim 38 further comprising
an alarm provision coordinated to the measurement processing unit of the temperature-humidity measurement cable.

41. The surveillance provision for containers of fluids according to claim 38 further comprising
a picture providing representation installed at an operating desk of a power plant and associated with the measurement value processing of the temperature-humidity measurement cable.

42. The surveillance provision for containers of fluids according to claim 3 wherein the temperature-humidity measurement cable is disposed in a gully in the floor of a power plant for the detection of the presence of liquids.

43. The surveillance provision for containers of fluids according to claim 42 wherein the temperature-humidity measurement cable is disposed at an insertion body placed into the gully.

44. The surveillance provision for containers of fluids according to claim 43 wherein from a contact to only a slight gap is present between a container wall and the temperature-humidity measurement cable disposed at the insertion body.

45. The surveillance provision for containers of fluids according to claim 43 wherein the temperature-humidity measurement cable is disposed at a circumferential recess of the insertion body such that the outer diameter is equal to or slightly larger than the diameter of the insertion body in the region of the temperature-humidity measurement cable.

46. The surveillance provision for containers of fluids according to claim 43 wherein the connection of the temperature-humidity cable is furnished substantially as a construction unit with a liquid sealing coupling plug of a measurement conduit disposed in a liquid sealing insulated receptacle in the insertion body.

47. The surveillance provision for containers of fluids according to claim 46 wherein the plug receptacle is maintained in the middle region of the insertion body via radial steadying support struts.

48. The surveillance provision for containers of fluids according to claim 43 wherein the insertion body with the temperature-humidity measurement cable is supported in a tubular container part, which is disposed at a ring insertable into the gully.

49. The surveillance provision for containers of fluids according to claim 48 wherein the tubular container part in disposed substantially off center at an inner surface of the ring and is provided here with a groove formation for feeding in of the liquid.

50. The surveillance provision for containers of fluids according to claim 43 further comprising
a measurement processing unit comprising transducers, evaluation electronics, control systems and an alarm provision is coordinated to the temperature-humidity measurement cable disposed at the insertion body located in the gully.

51. The surveillance provision for containers of fluids according to claim 3 further comprising a circuit for applying an electrical voltage to the resistance wire of the temperature-humidity measurement cable such that the resistance wire is formed as an electrical heating element for the drying of possible humidity parts in the temperature-humidity measurement cable or in its environment.

52. A method employing a measurement cable for surveillance of a pipe-like container containing a fluid medium comprising
separating two substantially parallel running electrical conductor wires with an interposed hygroscopic insulating means for humidity control and for spacing said conductor wires at a predetermined distance relative to each other;
surrounding the wires and the hygroscopic insulating means with a permeable insulator;
running substantially in parallel to the electrical conductor wires a resistance wire temperature sensor helically surrounding the conductor wires at a preselected distance; and covering the wires and insulation in order to obtain a temperature-humidity measurement cable.

53. The method for surveillance of a container containing a fluid medium according to claim 52 further comprising providing the hygroscopic insulating means of glass filament insulation.

54. The method for surveillance of a container containing a fluid medium according to claim 52 further comprising attaching the temperature-humidity measurement cable to a flat band type of support means.

55. The method for surveillance of a container containing a fluid medium according to claim 52 further comprising attaching a sealing strip between the flat band carrying the temperature-humidity measurement cable and the covering of the thermal insulation.

56. The method for surveillance of a container containing a fluid medium according to claim 52 further comprising surrounding the temperature-measurement cable with an insertion body; and placing the insertion body in a gully.

57. A method for surveillance of a container containing a fluid medium according to claim 52 further comprising applying an electrical voltage by circuit means to the resistance wire of the temperature-humidity measurement cable wherein the resistance wire is formed as an electrical heating element for the drying of possible humidity parts in the temperature-humidity measurement cable or in its environment.

* * * * *